(12) United States Patent
Campbell et al.

(10) Patent No.: US 9,625,398 B1
(45) Date of Patent: Apr. 18, 2017

(54) CROSS SECTIONAL DEPTH COMPOSITION GENERATION UTILIZING SCANNING ELECTRON MICROSCOPY

(71) Applicant: INTERNATIONAL BUSINESS MACHINES CORPORATION, Armonk, NY (US)

(72) Inventors: Eric J. Campbell, Rochester, MN (US); Sarah K. Czaplewski, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/992,144

(22) Filed: Jan. 11, 2016

(51) Int. Cl.
*G01N 23/225* (2006.01)
*G01B 15/02* (2006.01)

(52) U.S. Cl.
CPC ......... *G01N 23/2252* (2013.01); *G01B 15/02* (2013.01); *G01N 2223/304* (2013.01); *G01N 2223/633* (2013.01)

(58) Field of Classification Search
USPC ................. 250/310, 306, 307, 398
See application file for complete search history.

(56) References Cited

U.S. PATENT DOCUMENTS

| 5,210,414 | A | * | 5/1993 | Wallace | G01N 1/02 250/307 |
|---|---|---|---|---|---|
| 6,353,222 | B1 | | 3/2002 | Dotan | |
| 7,186,977 | B2 | | 3/2007 | Martin et al. | |
| 8,878,130 | B2 | | 11/2014 | Inada et al. | |
| 2012/0316855 | A1 | | 12/2012 | Park et al. | |
| 2015/0243477 | A1 | | 8/2015 | Stone et al. | |

FOREIGN PATENT DOCUMENTS

| EP | 2444991 A1 | 4/2012 |
|---|---|---|
| JP | 2-21549 A | 1/1990 |
| JP | 5423612 B2 | 2/2014 |

* cited by examiner

*Primary Examiner* — Kiet T Nguyen
(74) *Attorney, Agent, or Firm* — Tutunjian & Bitetto, P.C.; Joseph Petrokaitis

(57) ABSTRACT

A method for generating cross-sectional profiles using a scanning electron microscope (SEM) includes scanning a sample with an electron beam to gather an energy-dispersive X-ray spectroscopy (EDS) spectrum for an energy level to determine element composition across an area of interest. A mesh is generated to locate positions where a depth profile will be taken. EDS spectra are gathered for energy levels at mesh locations. A number of layers of the sample are determined by distinguishing differences in chemical composition between depths as beam energies are stepped through. A depth profile is generated for the area of interest by compiling the number of layers and the element composition across the mesh.

6 Claims, 5 Drawing Sheets

CROSS SECTIONAL DEPTH COMPOSITION GENERATION UTILIZING SCANNING ELECTRON MICROSCOPY

BACKGROUND

Technical Field

The present invention relates to characterizing layers of an object, and more particularly to systems and methods for generating cross-sectional composition and structural information using a scanning electron microscope (SEM).

Description of the Related Art

A scanning electron microscope (SEM) produces images of a sample or specimen by scanning with a focused beam of electrons. The electrons interact with atoms in the sample and produce signals that include information about a sample's surface topography and composition. An electron beam is scanned, and its position is combined with a detected signal to produce an image. SEM can achieve resolutions of better than 1 nanometer.

The electron beam may have an energy ranging from 0.2 keV to 40 keV and is focused by one or more condenser lenses. The beam scans in a raster pattern over an area of a sample. SEM can provide several items of data at each pixel. One example includes energy-dispersive X-ray spectroscopy (EDS). An EDS detector may be employed for elemental analysis to analyze an intensity and spectrum of electron-induced luminescence in specimens. The spectra signals can be color coded, so that differences in the distribution of the various components of the specimen can be seen clearly and compared.

In many applications, specimens are cross-sectioned to determine constituent structures and materials. In many instances, the specimens to be cross-sectioned are too fragile or too small to deconstruct or cross-section, or the specimens need to be preserved for other analyses where non-destructive testing is needed.

SUMMARY

A method for generating cross-sectional profiles using a scanning electron microscope (SEM) includes scanning a sample with an electron beam to gather an energy-dispersive X-ray spectroscopy (EDS) spectrum for at least one energy level to determine element composition across an area of interest. A mesh is generated to locate positions where a depth profile will be taken. EDS spectra is gathered for a plurality of energy levels at a plurality of mesh locations. A number of layers is determined by distinguishing differences in chemical composition between depths as beam energies are stepped through. A depth profile is generated for the area of interest by compiling the number of layers and the element composition across the mesh.

Another method for generating cross-sectional profiles using a SEM includes scanning a sample with an electron beam to gather an EDS spectrum for at least one energy level; identifying elements present in the sample using the EDS spectrum; generating a mesh on a region of interest in a SEM image of the sample to locate positions at intersections of the mesh where a depth profile will be taken; gathering EDS spectra for a plurality of energy levels at a plurality of mesh locations; determining a number of layers of the sample by distinguishing differences in chemical composition between depths of the sample as beam energies are stepped through; analyzing the chemical compositions between adjacent layers in the depth profile to determine whether a substantial difference exists; and if a substantial difference exists, generating a depth profile for the area of interest by compiling the number of layers and the element composition across the mesh.

A system for depth profiling a sample includes a SEM configured to scan a sample with an electron beam and at least one energy-dispersive X-ray spectroscopy (EDS) detector to gather EDS spectra for a plurality of energy levels to determine element composition and layer interfaces across an area of interest. A mesh is generated to locate positions where a depth profile will be taken. A processor is coupled to the SEM and includes an associated memory. A data reconstruction module is stored in the memory and is configured to gather EDS spectra for a plurality of energy levels at a plurality of mesh locations to determine a number of layers and their composition at each mesh location by distinguishing differences in chemical composition between depths as beam energies are stepped through. The data reconstruction module is further configured to generate a depth profile for the area of interest by compiling the number of layers and the element composition across the mesh.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The disclosure will provide details in the following description of preferred embodiments with reference to the following figures wherein.

DETAILED DESCRIPTION

Figure 1:
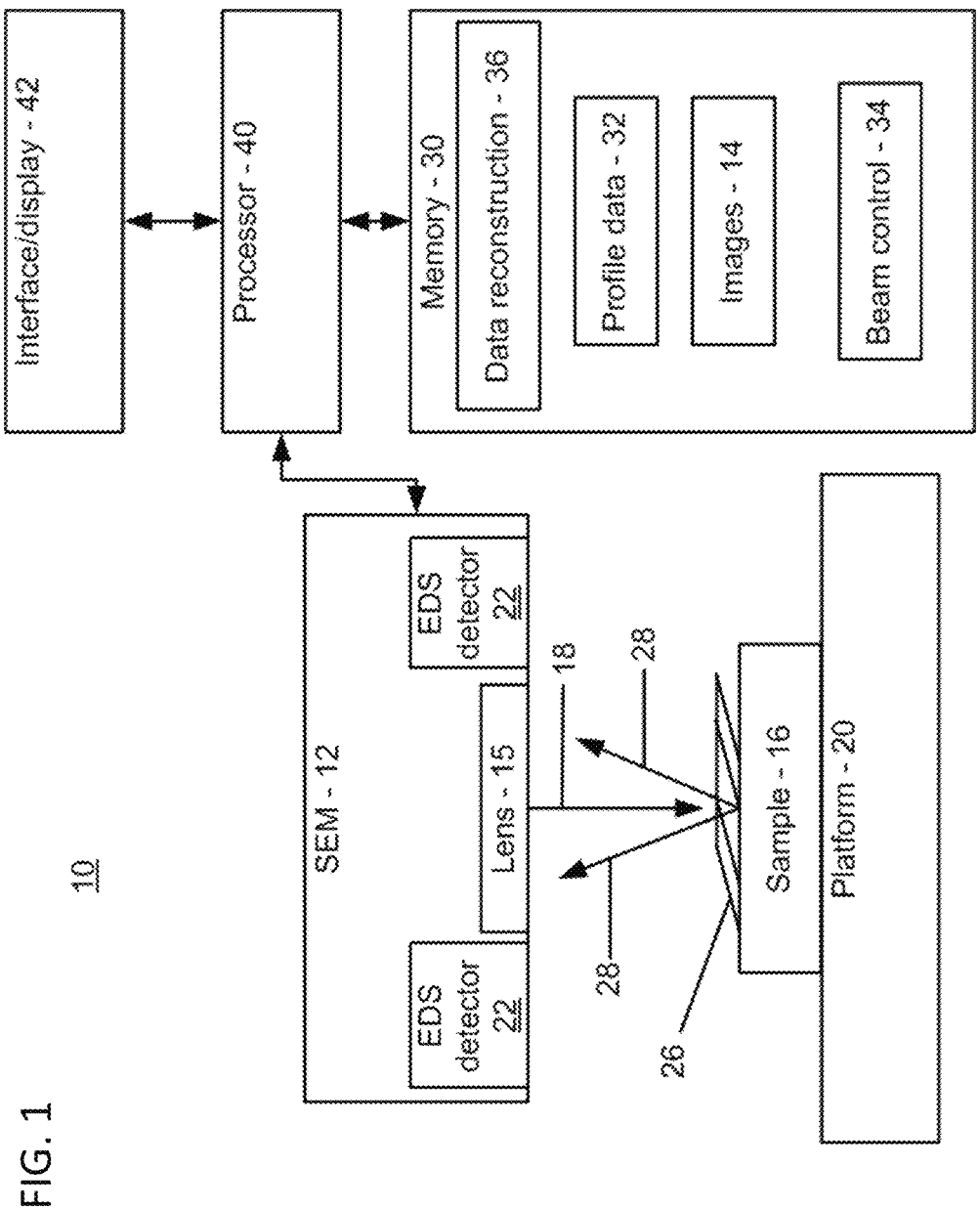
FIG. 1 is a block/flow diagram showing a scanning electron microscope (SEM) system in accordance with the present principles.

In accordance with the present principles, a scanning electron microscope (SEM) is employed to analyze materials to generate a cross-sectional depth composition into a surface of a sample. This is especially useful for small samples that are extremely difficult to manually cross-section and for specimens where non-destructive testing is needed. In one embodiment, a SEM creates a cross-sectional view into the sample by varying a beam voltage of the SEM. A cross-sectional depth composition of a surface is determined by performing a plurality of point scans using a SEM at various beam energy levels and then comparing electron dispersive X-ray spectroscopy (EDS) results at those various energy levels to create a depth composition.

In one illustrative method, beam penetration (which has a tear drop shape) is measured at various beam energy levels. As the beam energy is progressively increased or decreased, the composition that is measured by EDS detectors changes.

These changes will be employed to determine a depth, shape and/or composition of the layers or structures of the sample.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that the present invention will be described in terms of a given illustrative architecture; however, other architectures, structures, materials and process features and steps may be varied within the scope of the present invention.

It will also be understood that when an element such as a layer, region or object is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring now to the drawings in which like numerals represent the same or similar elements and initially to FIG. 1, an illustrative scanning electron microscope (SEM) system 10 is shown in accordance with the present principles. The SEM system 10 includes a scanning electron microscope 12 that produces images 14 of a sample 16 by scanning with a focused beam 18 of electrons. The electrons interact with atoms in the sample and produce signals that include information about a sample's surface topography and composition. An electron beam is scanned on a platform 20 on which the sample 16 is placed and moved. A positional relationship of the beam 18 and the information detected from the electrons to create a detected signal are employed to produce images 14 of the sample 16. The SEM 12 can produce an electron beam having an energy ranging from between about 0.2 keV to 40 keV, although other energies may be employed. The beam 18 is focused on the sample 16 by one or more condenser lenses 15 to a spot on the sample 16. The beam 18 may be scanned in a raster pattern or any other pattern over an area of sample 16.

A mesh or grid 26 is projected onto an image 14 or programmed into the platform 20 or SEM 12 to control motion of the sample 16 and/or electron beam 18. Intersections of the mesh or grid 26 are locations where the beam 18 will be parked while energy-dispersive X-ray spectroscopy (EDS) detectors 22 measure scattered X-rays to be analyzed. The X-ray spectroscopy data and position data will be stored in a memory 30 in a profile data structure 32. The memory 30 is coupled to a processor 40. The processor 40 carries out computations and system functions and may be employed to control SEM operations. The processor 40 and memory 30 may be integrated with the SEM 12 or may be part of an external computer system or network.

The profile data 32 is employed to identify a composition and structure of the sample 16 at each location. The EDS detector(s) 22 may be employed in elemental analysis to analyze an intensity and spectrum of electron-induced luminescence in the sample 16. This is performed by gathering EDS spectra from the detectors 22 and distinguishing differences between chemical compositions as the beam energy is increased or decreased. The beam energy is controlled relative to a plan stored in a beam control module 34. The beam control module 34 may randomly select a sequence of beam energies or may follow a determined protocol. The plan may be specific to a sample type, different grid locations or any other criteria. A data construction module 36 maps out the sample 16 using the data stored in the profile data structure 32.

The data reconstruction module 36, which is stored in the memory 30, is configured to gather EDS spectra for a plurality of energy levels at a plurality of mesh locations to determine a number of layers and their composition at each mesh location by distinguishing differences in chemical composition between depths as beam energies are stepped through. The data reconstruction module 36 is further configured to generate a depth profile for the area of interest by compiling the number of layers and the element composition across the mesh. The depth profile provides a virtual model of the sample.

The data construction module 36 may generate an image for display on a display/interface 42 to show a cross-sectional structure of the sample 16 using the EDS spectra signals. The display/interface 42 may include peripherals, such as a keyboard, mouse, microphone, etc. to enable input and output (e.g., speakers, display, etc.) for user interaction with the system 10.

Figure 2:
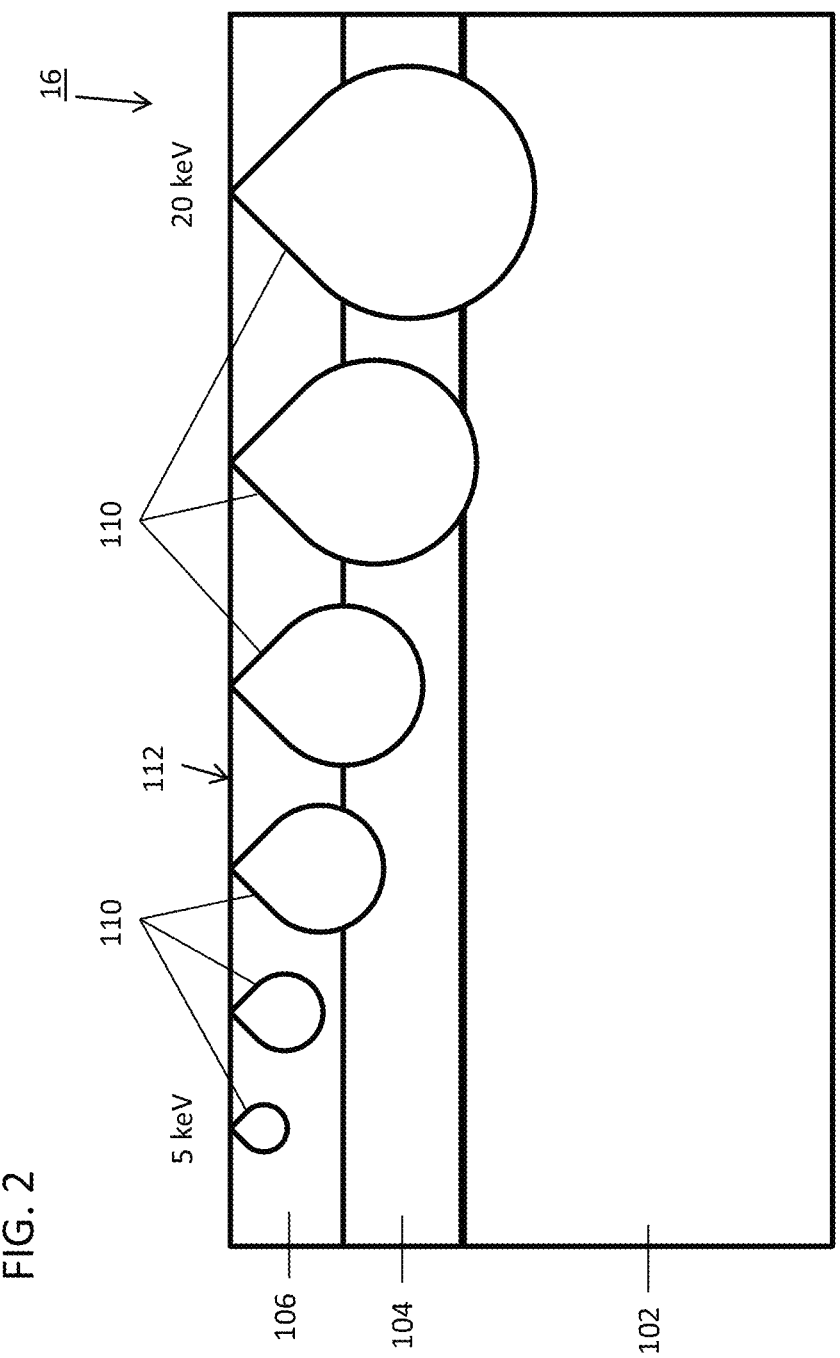
FIG. 2 is a cross-section of a sample showing beam penetration distributions in accordance with the present principles.

Referring to FIG. 2 with continued reference to FIG. 1, an illustrative cross-section of a sample 16 is shown in accordance with the present principles. In the illustrative embodiment, the sample includes three layers: a layer of copper 102, a layer of nickel 104 and a layer of gold 106. The layers 102, 104 and 106 may have different depths. A SEM employs beams having various energies, which range between 5 keV and 20 keV in this example.

When a primary electron beam 18 interacts with the sample 16, the electrons lose energy by repeated random scattering and absorption within a teardrop-shaped volume of the specimen known as an interaction volume 110, which extends from less than 100 nm to approximately 5 μm below a surface 112. The size of the interaction volume 110 depends on the electron's landing energy, the atomic number of the sample and the density of the material. The energy exchange between the electron beam 18 and the sample 16 results in the reflection of high-energy electrons by elastic scattering, emission of secondary electrons by inelastic scattering and the emission of electromagnetic radiation (including X-rays), each of which can be detected by specialized detectors including EDS detectors 22.

The beam current absorbed by the sample 16 can also be detected and used to create images of the distribution of specimen current. Electronic amplifiers of various types may be employed to amplify the signals, which are displayed as variations in brightness on a computer display 42. Each pixel of computer video memory is synchronized with a position of the beam 18 on the sample 16, and a resulting image is a distribution map of the intensity of the signal being emitted from the scanned area of the sample 16 and saved to memory 30 in a profile data structure 36 in computer storage.

A beam penetration depth X (μm) can be determined by relating beam energy $E_0$(keV) and material density p. A given sample may include multiple layers of material, and therefore beam penetration will change depending on sample composition. An equation (1) shows a relationship between beam energy $E_0$(keV) and beam penetration depth X (μm) where p is the density:

$$X (\mu m)=(0.1 E_0^{1.5})/p \quad (Eq. 1)$$

In other embodiments, Monte Carlo simulation may be employed to determine beam penetration in a sample. Monte Carlo simulation models scattering paths through the materials and may employ a large population of scattering particles to map out a scatter profile for the particles. The Monte Carlo simulation results in plots tracing out paths that collectively resemble the tear-drop shape of beam penetration 110. From the beam penetration profile, whether computed or simulated, the materials and structures can be determined for the sample 16.

Figure 3:
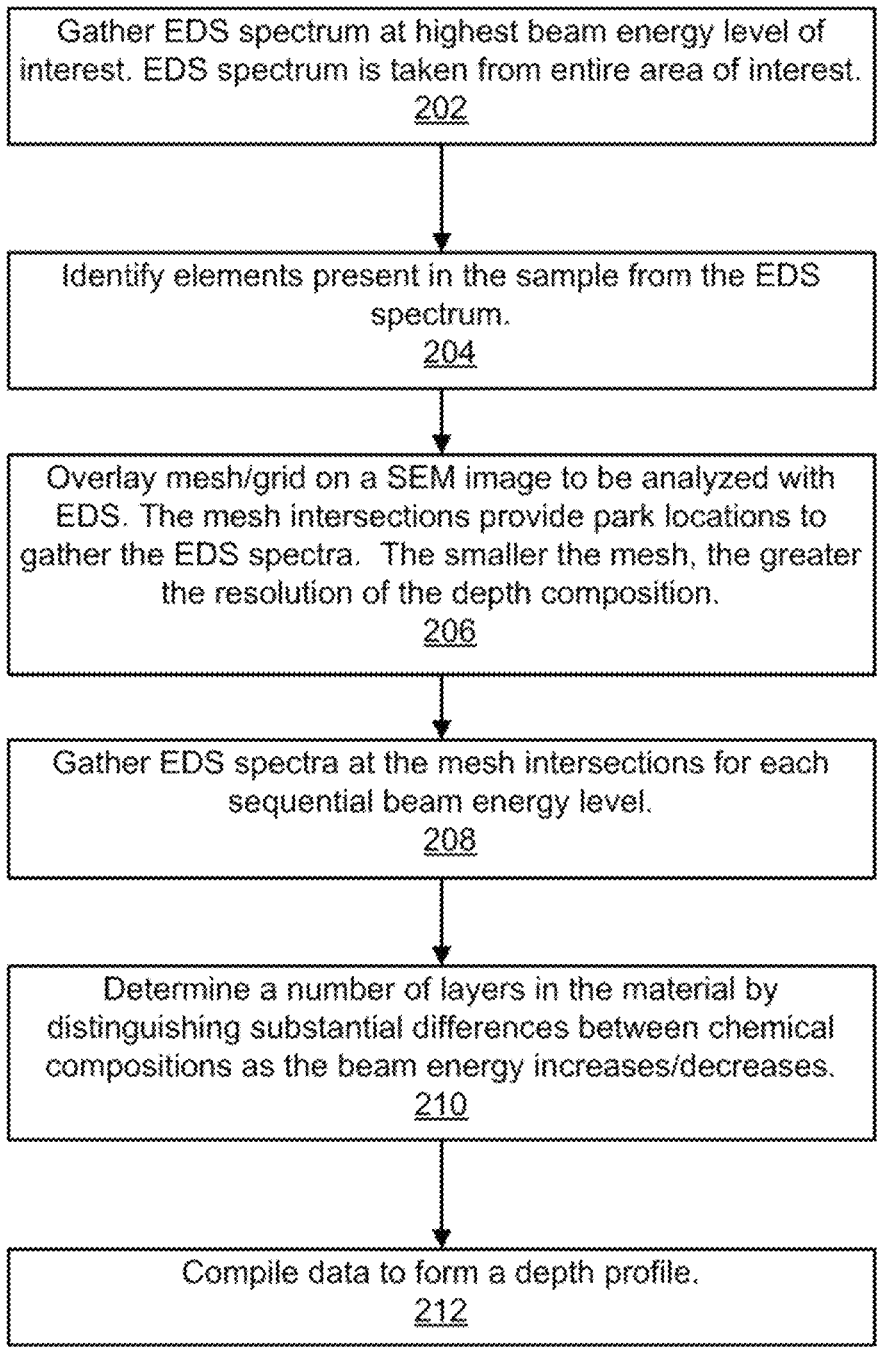
FIG. 3 is a block/flow diagram showing a method for gathering a depth composition profile of a sample using a SEM in accordance with one illustrative embodiment.

Referring to FIG. 3, a method for gathering a depth composition profile of a sample using a SEM is shown in accordance with one illustrative example. In block 202, an EDS spectrum is gathered at a highest energy level (e.g., 20 keV, or 40 keV ) of interest. The EDS spectrum is taken from the entire area of interest. The EDS spectrum is mapped with position in the area of interest. In block 204, the elements included in the sample are identified using the EDS spectra. The identified elements may be mapped with position in the area of interest. In block 206, a mesh or grid is overlaid onto the sample area to be analyzed with EDS. The mesh intersections are where the beam will park to take the EDS spectrum. A resolution of the depth composition will be greater with smaller mesh size.

In block 208, EDS spectra are gathered at the mesh intersections for each sequential beam energy level. In a given method, the number of beam energy levels may be selected based upon knowledge of the sample, the size of the sample, the number of layers in the sample, etc. In one embodiment, the number of different energy levels may be three, in other embodiments, the number of energy levels may be much higher. The energy levels may be incremented or decremented by a discrete amount for each iteration (e.g., 5 keV).

In block 210, a number of layers in the materials may be determined by distinguishing substantial differences between chemical compositions of the layers as the beam energy increases or decreases. The data profile information is stored. In block 212, the profile data is compiled to form a depth profile across the area of interest. The compilation may be displayed to be viewed or analyzed. The present principles enable cross-sectioning of samples to determine constituent structures and materials, e.g., that are too fragile or too small to deconstruct or cross-section mechanically.

Figure 4:
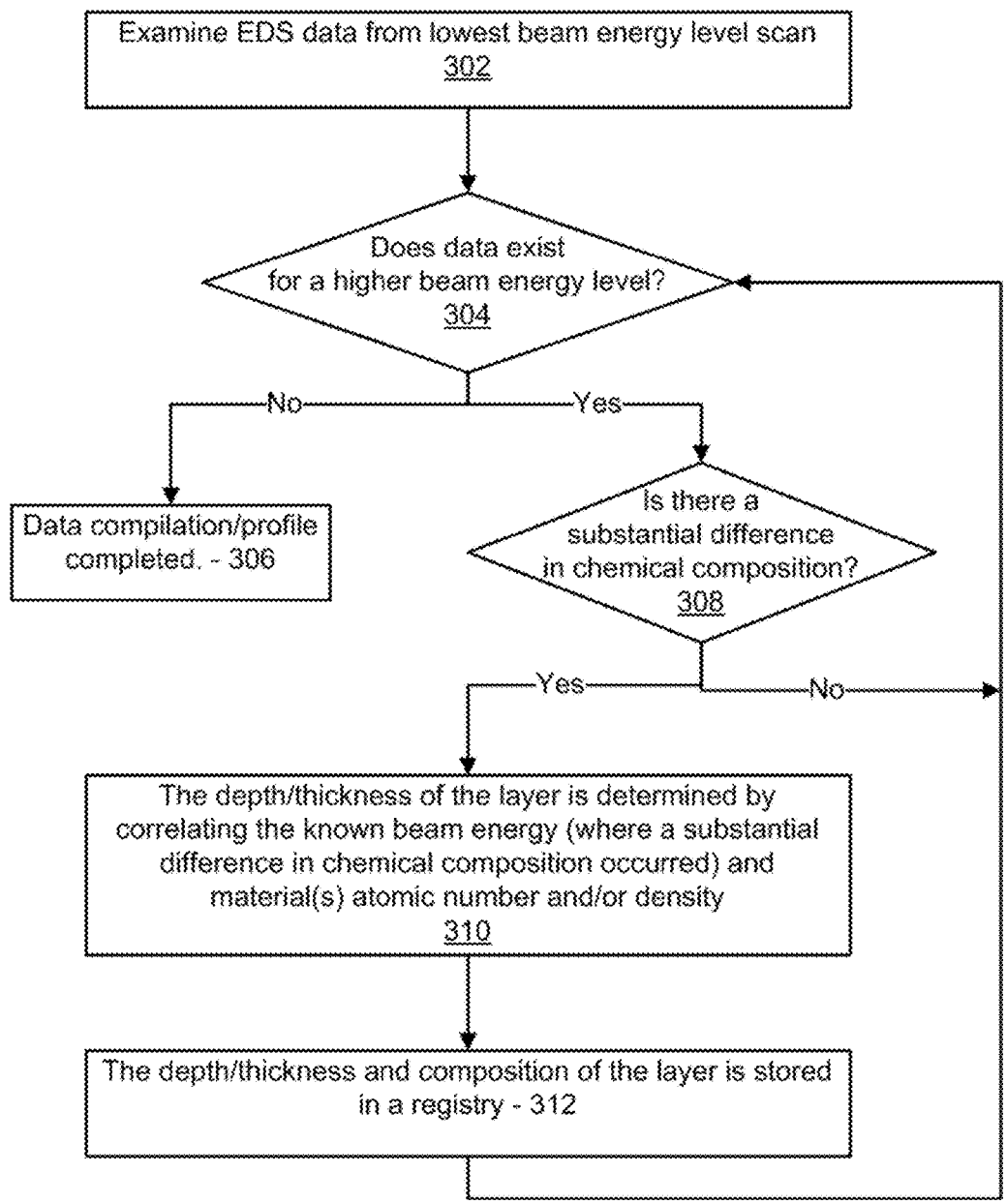
FIG. 4 is a block/flow diagram showing a method for generating a depth profile from energy-dispersive X-ray spectroscopy (EDS) data/spectra for a sample using a SEM in accordance with one illustrative example.

Referring to FIG. 4, a method for generating a depth profile from EDS data/spectra for a sample using a SEM is shown in accordance with one illustrative example. In block 302, EDS data from a lowest energy level scan (of a set of energy levels selected for generating the profile in FIG. 3) is examined, e.g., for the profile data structure. In block 304, a determination is made as to whether EDS data for a higher level scan exists. If no, the data compilation is completed in block 306. Otherwise, if a higher level scan exists, a determination is made in block 308 as to whether there is a substantial difference in chemical composition. A substantial difference may be measured in accordance with user defined criteria. In one example, substantial may be determined based upon a difference in element or atomic percent of an element and/or the detection of a previously undetected element.

If there is not a substantial difference in chemical composition, the path returns to block 304 and continues. If there is a substantial difference in chemical composition, in block 310, a depth or thickness of the layer or layers are determined by correlating the known beam energy with atomic number and/or density of the material(s). The depth is determined at the point where the chemical composition changed, which provides an indication where the layer interface exists between materials of different chemical compositions.

In block 312, the depth or thickness of the layer or layers are stored in a registry or data profile structure. Then, the path returns to block 304 to continue through other energy levels for the area of interest.

Figure 5:
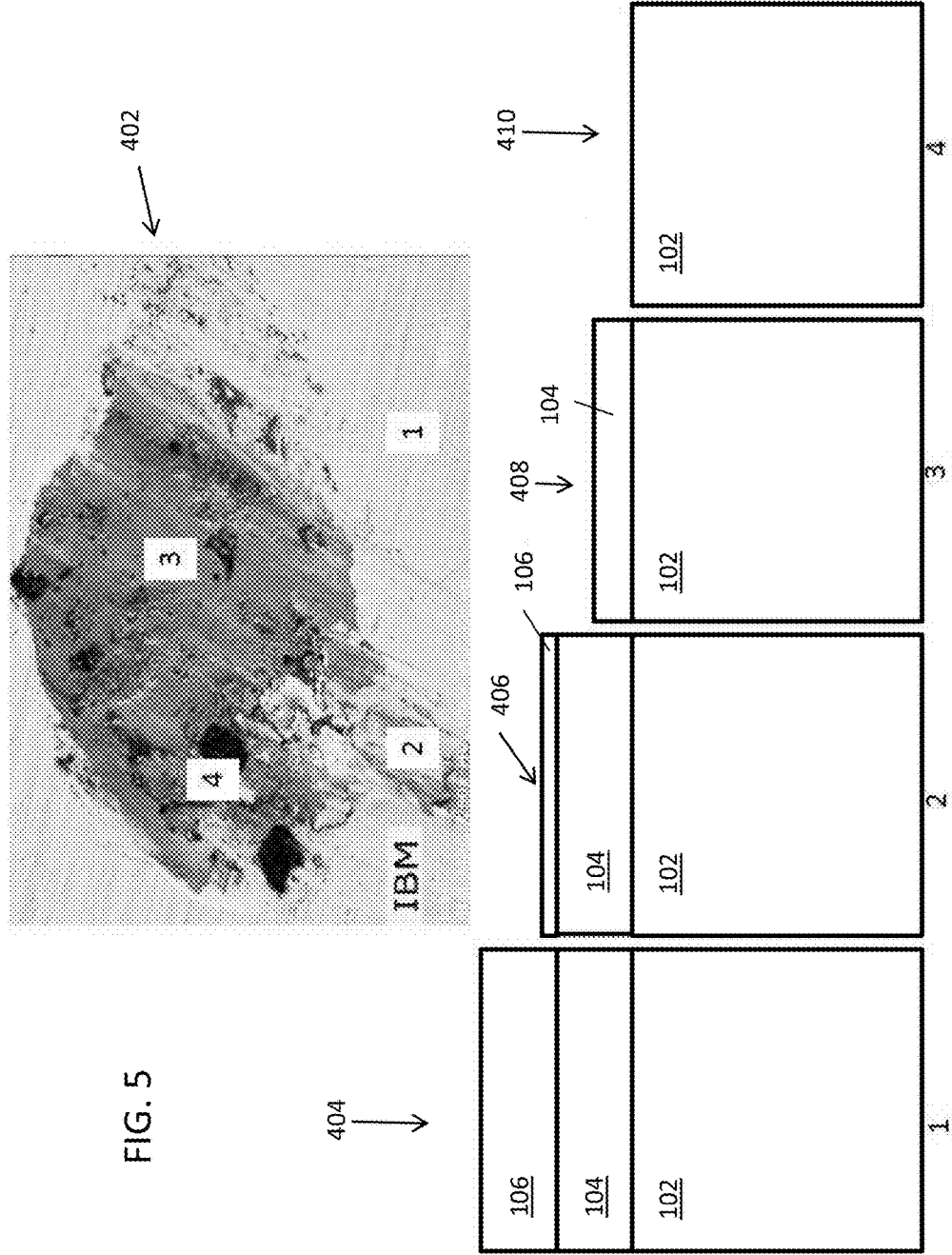
FIG. 5 is an image of a sample with four positions marked and depth profiles indicated for each of the four positions in accordance with one illustrative embodiment.

Referring to FIG. 5, an illustrative example showing a sample 402 having different cross-section profiles at position 1-4 is shown to demonstrate the present principles. In accordance with the present principles, a cross-section is generated for the sample 402 including, e.g., interfaces between different materials using a plurality of different electron beam energies as described above. As described, this is useful when the sample is too small to be cross-sectional mechanically or has to be preserved (no damage). The sample shown in FIG. 5 is an electrical connector that has experienced wear (e.g., wear due to one-time or repeated use over time). Some of the material is abraded away or damaged and some materials is pristine (see positions 1-4). The present principles employ electron beams of varying energies to reconstruct the cross-section of the electrical connector at each position (1-4). In this way, the sample can be measured without destruction and mechanical cross-sectioning is avoided (e.g., no sawing through to cross-section the sample).

Beam penetration depth can be determined by relating beam energy and sample composition as described above, e.g., by equation or Monte Carlo simulation. By calculating or simulating the beam penetration depth and correlating the depth with the known compositions at various beam energies, a cross sectional depth composition can be created. An output of the depth composition includes layers 102, 104 and 106 at different positions 1-4 on the sample 402. The sample 402 is an example showing wear experienced by an electrical connector in an SEM image.

By scanning the positions 1-4 at various beam energies, the present principles are able to generate a depth profile in the wear area of sample 402. Positions 1-4 in the sample 402 are examples of areas of interest in the wear spot. Example depth profiles 404, 406, 408 and 410 corresponding with regions 1-4 are shown. Depth profile 404 (position 1) includes no wear and has 30 micro-inches of gold of a top layer 106 intact. Depth profile 406 (position 2) shows signs of wear with only 5 micro-inches of gold remaining from the top layer 106. Depth profile 408 (position 3) has the gold layer 106 completely worn away and only 15 micro-inches of a 30 micro-inch nickel layer 104 remaining. Depth profile 410 (position 4) has the gold layer 106 and nickel layer 104 completely worn away, and a copper layer 102 is exposed.

Having described preferred embodiments for cross sectional depth composition generation utilizing scanning electron microscopy (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A system for depth profiling a sample, comprising:
  a scanning electron microscope (SEM) configured to scan a sample with an electron beam;
  at least one energy-dispersive X-ray spectroscopy (EDS) detector to gather EDS spectra for a plurality of energy levels to determine element composition and layer interfaces across an area of interest;
  a mesh generated to locate positions where a depth profile will be taken;
  a processor coupled to the SEM and including an associated memory; and
  a data reconstruction module stored in the memory and configured to gather EDS spectra for a plurality of energy levels at a plurality of mesh locations to determine a number of layers and their composition at each mesh location by distinguishing differences in chemical composition between depths as beam energies are stepped through, the data reconstruction module further configured to generate a depth profile for the area of interest by compiling the number of layers and the element composition across the mesh.

2. The system as recited in claim 1, wherein the number of beam energies are stepped through a set step size.

3. The system as recited in claim 1, wherein the depth profile is determined by correlating beam energy with atomic number and/or material density to determine a depth of an interface between materials of different chemical compositions.

4. The system as recited in claim 1, further comprising a profile data structure for storing information for the depth profile.

5. The system as recited in claim 1, wherein the depth profile provides a virtual model of the sample.

6. The system as recited in claim 1, wherein the mesh includes a grid size, the grid size being adjustable such that an adjustment to the grid size controls a resolution of the depth profile.

* * * * *